US006648223B2

(12) United States Patent
Boukhny et al.

(10) Patent No.: US 6,648,223 B2
(45) Date of Patent: *Nov. 18, 2003

(54) SURGICAL SYSTEM

(75) Inventors: Mikhail Boukhny, Laguna Beach, CA (US); Bruno Dacquay, Irvine, CA (US); Douglas M. Fanney, San Clemente, CA (US); Michael A. Southard, Arlington, TX (US); David Thoe, Aliso Viejo, CA (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/272,023

(22) Filed: Oct. 16, 2002

(65) Prior Publication Data

US 2003/0178489 A1 Sep. 25, 2003

Related U.S. Application Data

(63) Continuation-in-part of application No. 10/103,382, filed on Mar. 21, 2002.

(51) Int. Cl.⁷ ............................................... G06F 17/60
(52) U.S. Cl. ....................................................... 235/385
(58) Field of Search ................................. 235/385, 383, 235/462.13; 283/74, 81; 206/349, 363, 370; 705/28, 29

(56) References Cited

U.S. PATENT DOCUMENTS

| 4,833,306 | A | * | 5/1989 | Milbrett ........................ 235/375 |
| 4,844,259 | A | * | 7/1989 | Glowczewskie et al. .... 206/370 |
| 5,048,870 | A | | 9/1991 | Mangini et al. |
| 5,283,943 | A | * | 2/1994 | Aguayo et al. ................ 29/701 |
| 5,408,076 | A | * | 4/1995 | Griffanti ....................... 235/375 |
| 5,488,223 | A | * | 1/1996 | Austin et al. ................ 235/375 |
| 5,724,244 | A | * | 3/1998 | Yabuki ......................... 705/400 |
| 5,845,264 | A | * | 12/1998 | Nellhaus ....................... 705/28 |
| 5,899,674 | A | | 5/1999 | Jung et al. |
| 6,005,482 | A | * | 12/1999 | Moran et al. ............. 340/568.8 |
| 6,036,458 | A | | 3/2000 | Cole et al. |
| 6,059,544 | A | | 5/2000 | Jung et al. |
| 6,098,892 | A | * | 8/2000 | Peoples, Jr. ................. 235/494 |
| 6,155,975 | A | | 12/2000 | Urich et al. |
| 6,204,491 | B1 | * | 3/2001 | Montani ....................... 219/679 |
| 6,238,623 | B1 | | 5/2001 | Amhof et al. |
| 6,341,726 | B1 | * | 1/2002 | Castanedo et al. ...... 235/462.13 |
| 2001/0006818 | A1 | | 7/2001 | Amhof et al. |

FOREIGN PATENT DOCUMENTS

| EP | 550124 A2 | * | 7/1993 | ............. F24C/7/08 |
| JP | 09205291 A | * | 8/1997 | ........... H05K/13/00 |

* cited by examiner

*Primary Examiner*—Diane I. Lee
(74) *Attorney, Agent, or Firm*—Jeffrey S. Schira

(57) ABSTRACT

A surgical system console having an electronic identification system, such as a bar code scanner, magnetic reader or other sensing device (e.g., optical, magnetic or other system) system that works in conjunction with a unique identifier on the surgical pak so as to identify the contents of the pak to the surgical console control (e.g., CPU). That information can be used for a variety of further activities, such as inventory management, product usage, traceability, patient billing, collection of statistical data, OR support, automatic setting of the surgical operating parameters by the surgical console, servicing and to print out the contents of the surgical pak on a list or any other recordable media (e.g., DVD, CD-ROM, floppy disk, hard drive, ZIP drive.

24 Claims, 6 Drawing Sheets

SURGICAL SYSTEM

This application is a continuation in part application of U.S. patent application Ser. No. 10/103,382, filed Mar. 21, 2002, currently co-pending.

BACKGROUND OF THE INVENTION

This invention relates generally to the field of cataract surgery and more particularly to surgical systems used during the phacoemulsification technique of cataract removal.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, while other lens removal modalities are being introduced, the majority of cataractous lenses are still removed by a surgical technique called ultrasound phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly. The disposable portions of the system, such as the cutting tips, fluid tubings, cassette, drapes and sleeves, are generally sold together as a complete unit in the form of a surgical pak.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

With the advances that have been made in the last few years in digital circuitry, manufacturers are able to design and built surgical instruments that can automatically change the operating parameters to suit special techniques or situations. Operating parameters such as aspiration fluid flow rate and vacuum, irrigation fluid flow rate and pressure and handpiece power and duty cycle can all be preprogrammed for a specific surgeon or surgical procedure. In addition, the various cutting tips, sleeves, tubings and cassettes can be customized to suit the techniques being used by the surgeon. In order optimize the system, it is important that the operating parameters, tips, sleeves , tubings and cassettes all be designed to work together. With the various disposable products that are available today, it is often difficult for the surgeon to know if the operating parameters of the surgical console have been optimized for the contents of the surgical pak being used.

One prior art device illustrated in U.S. Pat. Nos. 5,899,674 and 6,059,544 (Jung, et al.) discloses a surgical cassette having an identification system that can be used by the surgical console to identify the type of cassette being used. Another similar device, illustrated in U.S. Pat. No. 6,036,458 (Cole, et al.), discloses a surgical cassette having an identification system that can be used by the surgical console to identify the type of cassette being used as well as how many times the cassette has been used. None of these references discloses a system wherein the surgical console can identify all of items contained in the surgical pak, and automatically adjust the operating parameters of the system for those contents.

Therefore, a need continues to exist for a system that can identify all of the contents of a surgical pak and automatically adjust the operating parameters of the system for those contents.

BRIEF SUMMARY OF THE INVENTION

The present invention improves upon the prior art by providing a surgical system console having an electronic identification system, such as a bar code scanner, magnetic reader or other sensing means (e.g., optical, magnetic or other system) system that works in conjunction with a unique identifier on the surgical pak so as to identify the contents of the pak to the surgical console control (e.g., CPU). That information can be used for a variety of further activities, such as inventory management, product usage, traceability, OR support, patient billing, collection of statistical data, automatic setting of the surgical operating parameters by the surgical console, servicing and to print out the contents of the surgical pak on a list or any other recordable media (e.g., DVD, CD-ROM, floppy disk, hard drive, ZIP drive).

Accordingly, one objective of the present invention is to provide a surgical system having a console with an electronic identification system.

Another objective of the present invention is to provide a surgical system having a console capable of identifying the contents of the surgical paks used throughout the procedure.

Another objective of the present invention is to provide a surgical system having a surgical pak having contents that are identifiable to the surgical console.

Still another objective of the present invention is to provide a surgical system wherein information from the contents of the surgical paks is identified to the surgical console, and the console uses this information for setting automatically the operating parameters to be used by the surgical console.

DETAILED DESCRIPTION OF THE INVENTION

Figure 1:
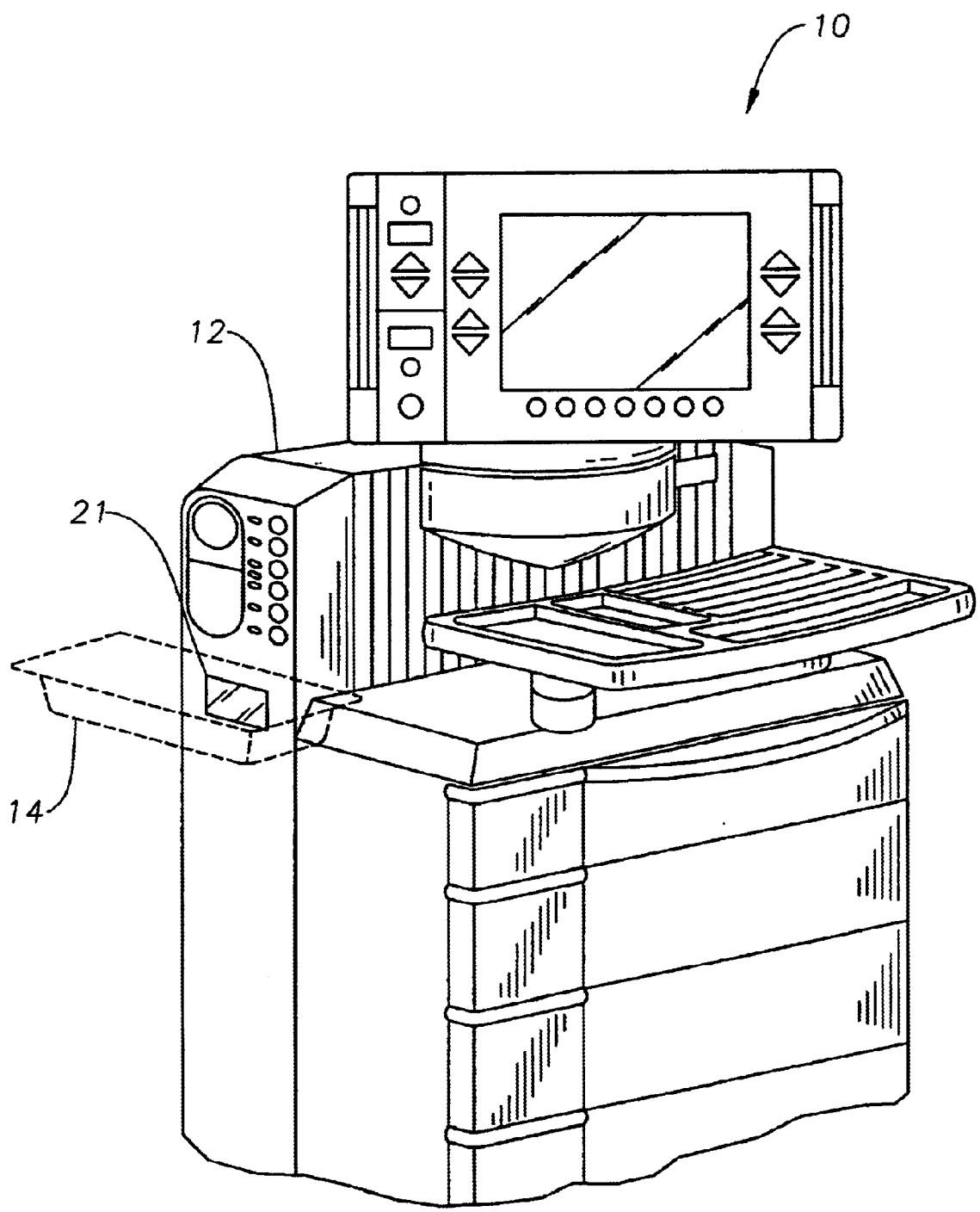
FIG. 1 is a perspective view of a surgical console that may be used with the present invention, showing the surgical pak in phantom.
Figure 2:
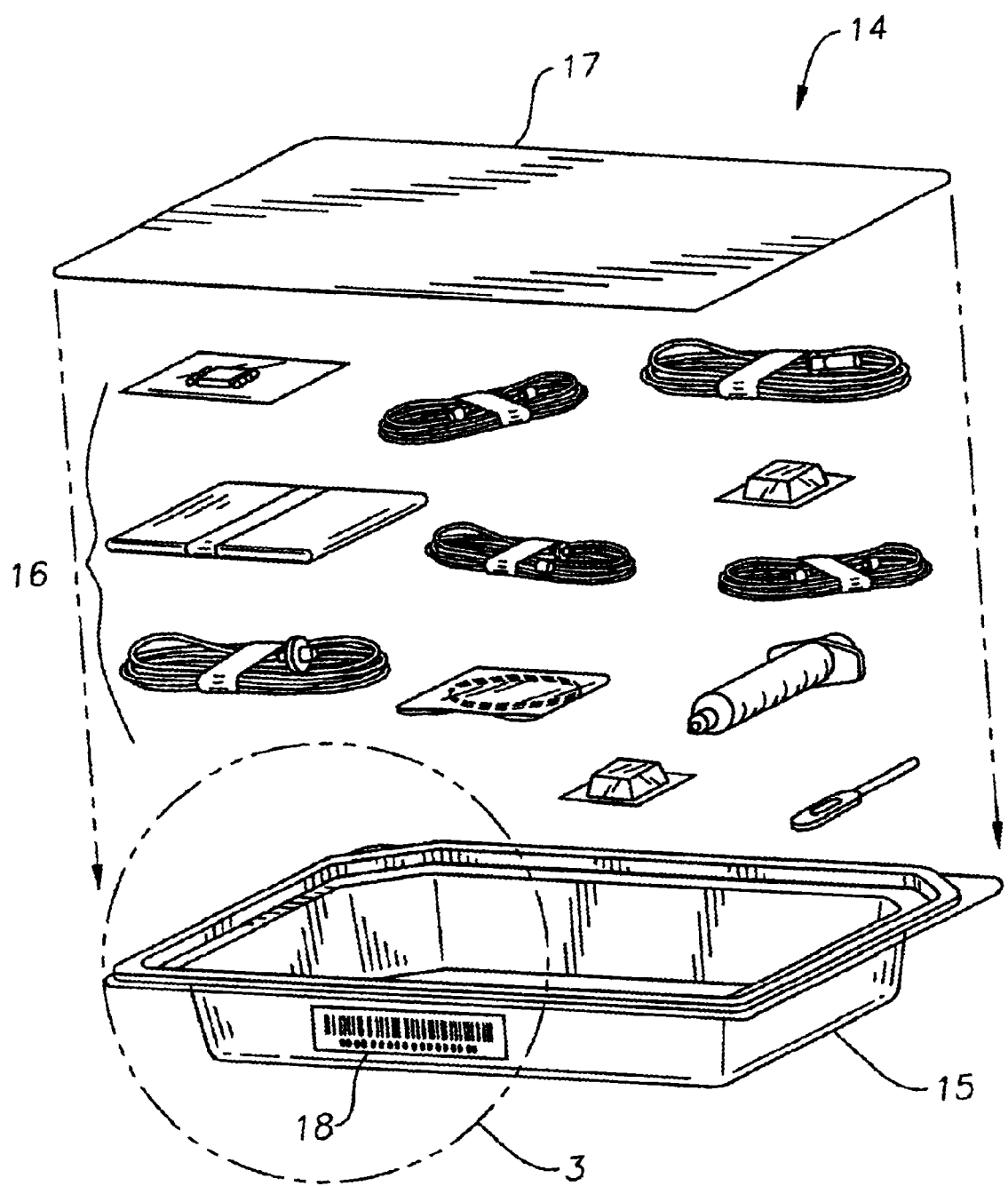
FIG. 2 is an exploded perspective view of a surgical pak that may be used with the present invention showing the various contents of the pak.

As best seen in FIG. 1, system 10 of the present invention generally includes surgical console 12 and surgical pak 14. Console 12 may be any suitably modified commercially available surgical console, such as the SERIES TWENTY THOUSAND® LEGACY® or ACCURUS® surgical systems available from Alcon Laboratories, Fort Worth, Tex. Pak 14 may be any suitably modified commercially available surgical, pak, such as those sold by Alcon Laboratories, Inc., Fort Worth, Tex. and, as best seen in FIG. 2, may contain any of a variety of components 16 required to perform a particular surgical procedure, such as cutting tips, sleeves, probes, cassettes, tubing sets, syringes, drapes, etc. Alternative paks 14 may contain pharmaceutical, viscoelastic agents or intraocular lenses. Components 16 are kept sterile in tray 15 by lid 17.

Figure 3:
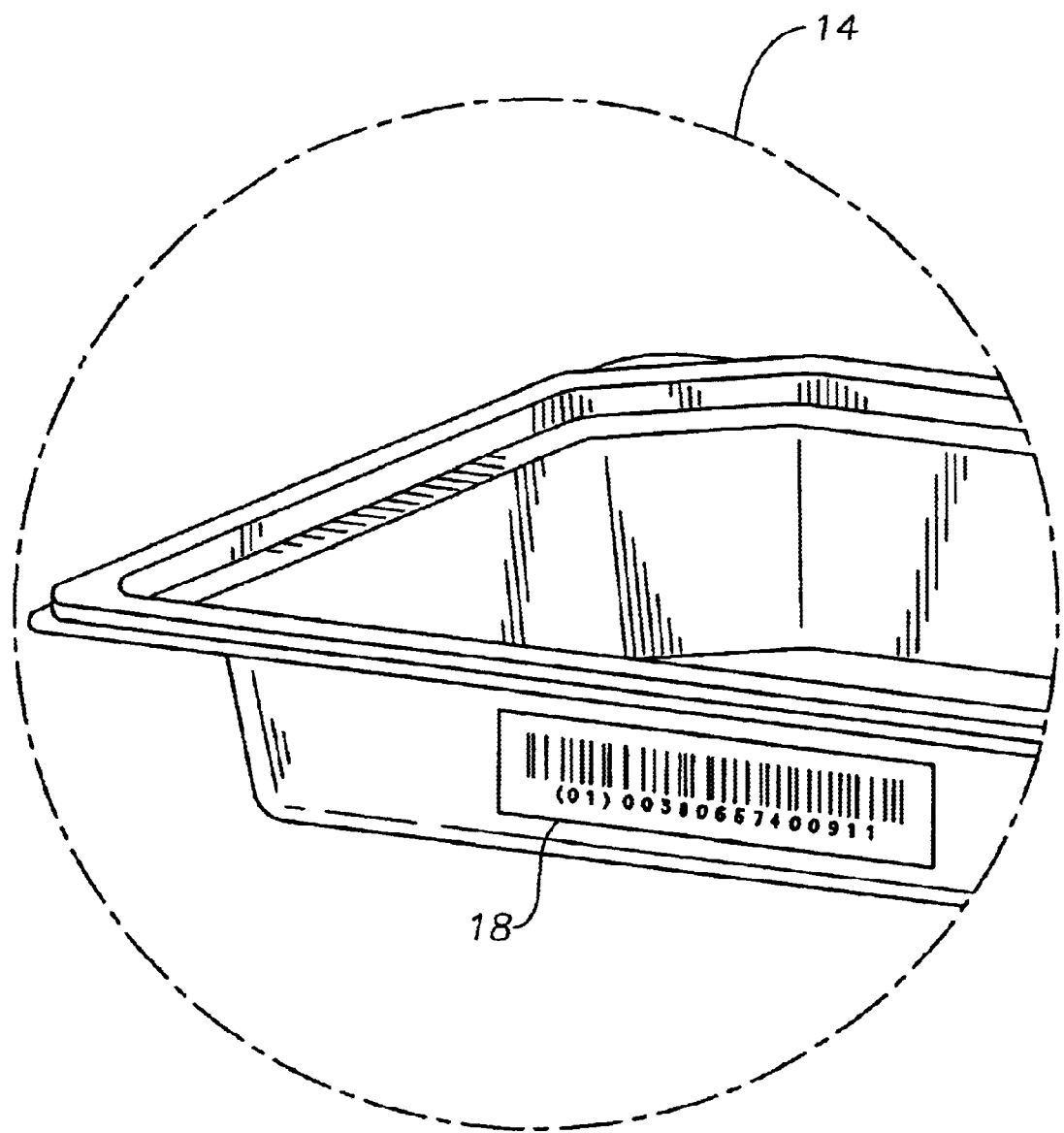
FIG. 3 is an enlarged perspective view of a surgical pak that may be used with the present invention taken at circle 3 on FIG. 2.

As best seen in FIG. 3, pak 14 contains identification device 18, such as a bar code, that identifies the contents of pak 14. Identification device 18 can either be external, such as with a bar code, or internal, such as with a magnetic device. In use, identification device 18 is presented to reader 21 on or connected to console 12. Reader 21 recognizes device 18, identifies pak 14 and components 16 contained in pak 14 and transmits this information to console 12. Console 12 uses this information, under appropriate software control as discussed below, to adjust automatically the operating parameters of console 12 to coincide with components 16 of pak 14 using factory or user programmable settings. Device 18 and reader 20 may be any of a variety of suitable electrical, magnetic or optical devices readily commercially available and well-known in the art.

Figure 4:
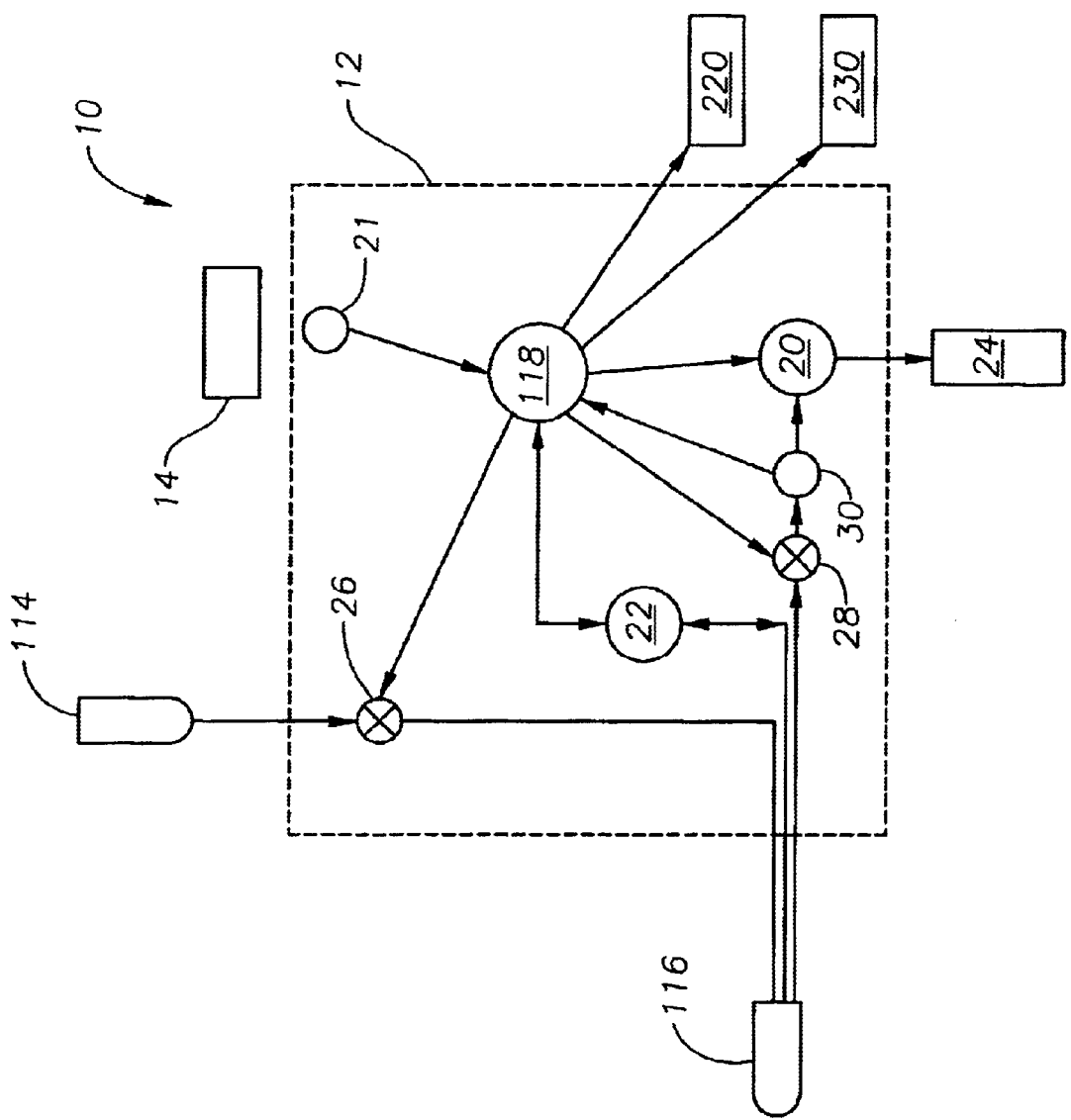
FIG. 4 is a schematic illustration of a surgical system console that may be used with the present invention.

As best seen in FIG. 4, control console 12 generally includes CPU 118, aspiration pump 20, handpiece power supply 22, infusion fluid valve 26, aspiration valve 28 and aspiration pressure sensor 30. Information supplied to CPU 118 from reader 21 is used to control aspiration valve 28, pump 20 and infusion fluid valve 26. CPU 118 also controls the power supplied to handpiece 116 by power supply 22. Aspirated fluid is directed by pump 20 to collection container 24.

Figure 5:
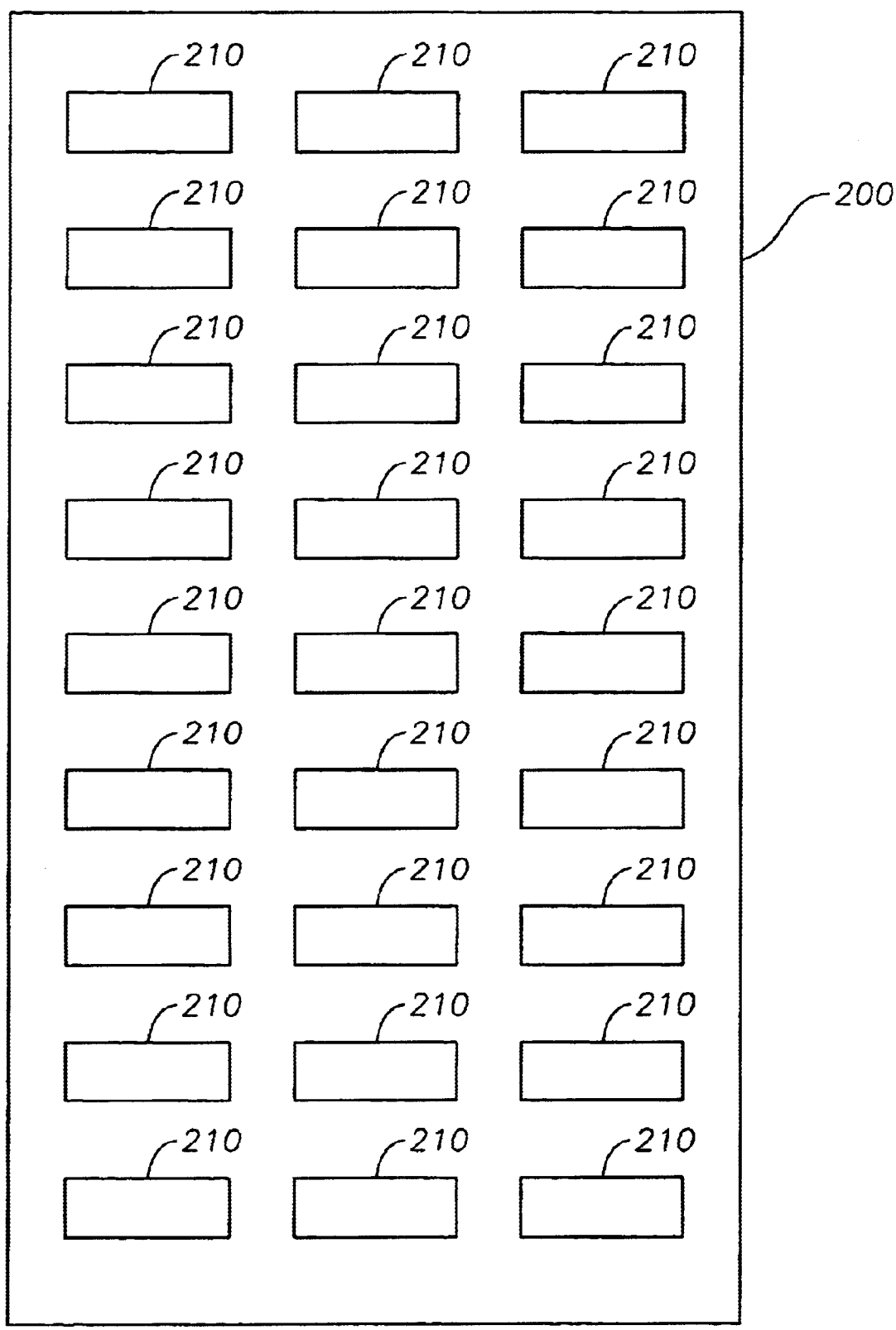
FIG. 5 is an illustration of a printout that may be obtained from the present invention.

In addition, control console 12 can signal printer 220 to print out a list of the contents of pak or paks 14 used during surgery. As seen in FIG. 5, list 200 may be in the form of a series of self-adhesive labels 210 that can be easily detached from list 200 and placed on the patient's medical chart so as to be able to track the various products, lenses, pharmaceuticals, etc. that were used during the surgical procedure. Printer 220 may communicate with control console 12 either via a hardwire connection, or a wireless connection (e.g. BLUETOOTH®).

System 10 may also be used for inventory control/ tracking by providing information regarding paks 14 or components 16 being used by the owners of system 10 to inventory management system or software 230, there being numerous inventory management software programs and systems being commercially available and well-known in the art. Inventory management system 230 can be used to re-order paks 14 and/or components 16 automatically. In addition, information such as the serial numbers, lot numbers or other information regarding paks 14 or components 16 can be tracked with system 10 and/or sent directing to the manufacturer(s) of paks 14 and/or components 16 through inventory management system 230. Inventory management system 230 may communicate with control console 12 either via a hardwire connection, or a wireless connection (e.g. BLUETOOTH®).

Figure 6:
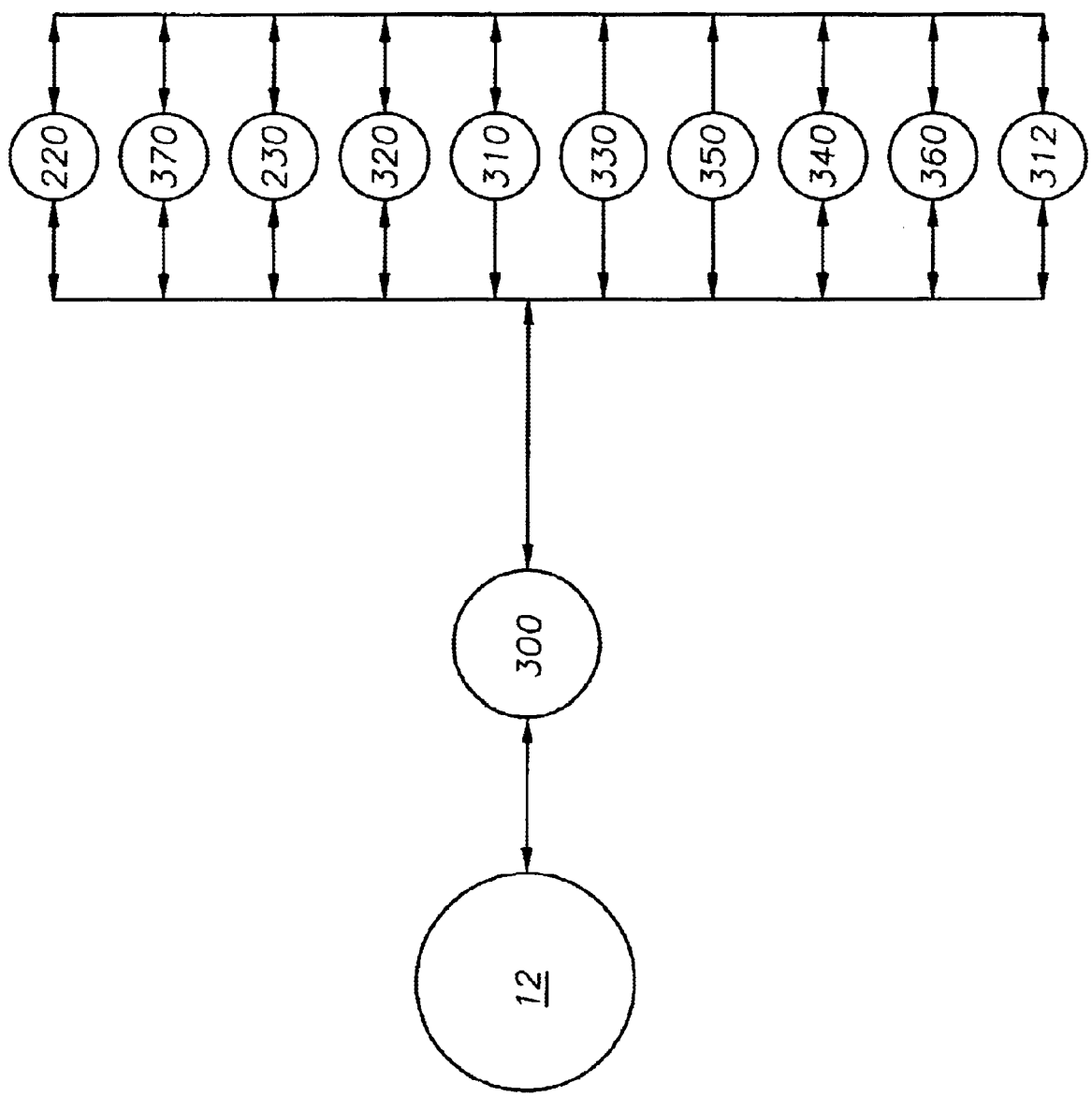
FIG. 6 is a schematic illustration of the system of the present invention.

As seen in FIG. 6, system 10 may contain appropriate hardware 300 (e.g., modem, ethernet card) and software to as to be electronically connected to communications devices external to console 12 within or outside of the surgical center, such as intranet or local area network (LAN) server 310, personal digital assistant (PDA) 320 or internet server 330, so as to provide a wide variety of information about the operation of console 12 and/or the surgical procedure(s) performed by console 12. Statistical data (e.g., patient data, performance parameters, surgical operating parameters (e.g., vacuum levels, ultrasound power, irrigation pressure), a video record of a surgical operation, or surgical operating times) may be transferred between remotely located console 12 and console 312, console 12 and surgical center database 340, and/or console 12 and manufacturer 350 of console 12 or stored on a suitable media, such as video recorder 360 or DVD/CD 370. Such information could assist in a variety of way, such as education, patient billing, technical services or patient quality assurance. Providing a record of such information may also allow the surgeon to review a surgical procedure post-operatively and thereby evaluate alternative surgical techniques and devices. Console 12 may also contain appropriate software that recognizes when console 12 requires service or repair and alerts automatically manufacturer 350.

In addition, system 10 allows for remote access to console 12 via hardware 300. Such remote access allows for the software used in console 12 to be updated remotely by manufacturer 350. In addition, service diagnoses made be made remotely. Training and other educational materials can be downloaded into console 12 and provided automatically whenever required or requested. Pre-operative patient data may be downloaded into console 12 so that the surgeon has a patient's complete medical record available during the surgical procedure. Package labeling, contraindications and directions for use for each surgical device to be used during the procedure, as well as the operation manual for console 12 can be downloaded onto console 12 and be available during the surgical procedure. Such information can be updated automatically by manufacturer 350.

This description is given for purposes of illustration and explanation. It will be apparent to those skilled in the relevant art that changes and modifications may be made to the invention described above without departing from its scope or spirit.

We claim:

1. A surgical procedure identification system, comprising:
   a) an ophthalmic surgical console for performing ophthalmic surgical procedures, the ophthalmic surgical console having a plurality of operating parameters and having a reader;
   b) at least one surgical pak containing a plurality of components;

c) an identification device associated with the surgical pak, the identification device capable of being recognized by the reader and providing information about the components contained in the surgical pak to the ophthalmic surgical console so as to adjust automatically at least one operating parameter of the ophthalmic surgical console; and d) a printer connected to the ophthalmic surgical console for printing out a list of the components contained in the surgical pak.

2. The surgical procedure identification system of claim 1 wherein the list is a plurality of labels.

3. The surgical procedure identification system of claim 1 wherein the identification device is a bar code and the reader is a bar code scanner.

4. The surgical procedure identification system of claim 1 wherein the connection between the ophthalmic surgical console and the printer is a wireless connection.

5. A surgical procedure identification system, comprising:

a) an ophthalmic surgical console for performing ophthalmic surgical procedures, the ophthalmic surgical console having a plurality of operating parameters and having a reader;

b) at least one surgical pak containing a plurality of components;

c) an identification device associated with the surgical pak, the identification device capable of being recognized by the reader and providing information about the components contained in the surgical pak to the ophthalmic surgical console so as to adjust automatically at least one operating parameter of the ophthalmic surgical console; and d) an inventory management system connected to the ophthalmic surgical console for tracking usage of the surgical pak and/or the components.

6. The surgical procedure identification system of claim 5 wherein the identification device is a bar code and the reader is a bar code scanner.

7. The surgical procedure identification system of claim 5 wherein the connection between the ophthalmic surgical console and the printer is a wireless connection.

8. A surgical procedure identification system, comprising:

a) an ophthalmic surgical console for performing ophthalmic surgical procedures, the ophthalmic surgical console having a plurality of operating parameters and having a reader;

b) at least one surgical pak containing a plurality of components;

c) an identification device associated with the surgical pak, the identification device capable of being recognized by the reader and providing information about the components contained in the surgical pak to the ophthalmic surgical console so as to adjust automatically at least one operating parameter of the console; and d) an external device electronically connected to the ophthalmic surgical console for receiving the information about the components contained in the surgical pak.

9. The surgical procedure identification system of claim 8 wherein the identification device is a bar code and the reader is a bar code scanner.

10. The surgical procedure identification system of claim 8 wherein the electronic connection between the control console and the external device is a wireless connection.

11. A method of operating a surgical system, comprising:

a) providing an ophthalmic surgical console for performing ophthalmic surgical procedures, the ophthalmic surgical console having at least one operating parameter, the ophthalmic surgical console capable of receiving and storing data and automatically adjusting the operating parameter based on the received and stored data;

b) connecting electronically the ophthalmic surgical console to a communications device, the device being located external to the surgical console;

c) transferring data electronically between the ophthalmic surgical console and the device.

12. The method of claim 11 wherein the device is a local area network server.

13. The method of claim 12 wherein the device communicates data received from the local area network server to the ophthalmic surgical console.

14. The method of claim 11 wherein the device is a personal digital assistant.

15. The method of claim 14 wherein the device communicates data received from the personal digital assistant to the ophthalmic surgical console.

16. The method of claim 11 wherein the device is an internet server.

17. The method of claim 16 wherein the device communicates data received from the internet server to the ophthalmic surgical console.

18. The method of claim 11 wherein the device is an intranet server.

19. The method of claim 18 wherein the device communicates data received from the intranet server to the ophthalmic surgical console.

20. The method of claim 11 wherein the data contains information about the components contained in a surgical pak containing a plurality of components.

21. The method of claim 20 wherein the device is a local area network server.

22. The method of claim 20 wherein the device is a personal digital assistant.

23. The method of claim 20 wherein the device is an internet server.

24. The method of claim 20 wherein the device is an intranet server.

* * * * *